United States Patent
Mao et al.

(10) Patent No.: US 11,697,014 B2
(45) Date of Patent: Jul. 11, 2023

(54) DEVICE FOR PREVENTING CONTAMINATION OF POSITIVE-PRESSURE CONNECTOR OF INDWELLING NEEDLE AND METHOD BASED ON SAME

(71) Applicants: SHANGHAI JIAOTONG UNIVERSITY, Shanghai (CN); SHANGHAI GOLDEN PHARMATECH CO., LTD., Shanghai (CN)

(72) Inventors: Zhenmin Mao, Shanghai (CN); Xiaoping Zhan, Shanghai (CN); Yan Long, Shanghai (CN); Chaoting Wang, Shanghai (CN)

(73) Assignees: SHANGHAI JIAO TONG UNIVERSITY, Shanghai (CN); SHANGHAI GOLDEN PHARMATECH CO., LTD., Shanghai (CN)

( * ) Notice: Subject to any disclaimer, the term of this patent is extended or adjusted under 35 U.S.C. 154(b) by 1030 days.

(21) Appl. No.: 16/473,626

(22) PCT Filed: Aug. 25, 2017

(86) PCT No.: PCT/CN2017/099018
§ 371 (c)(1),
(2) Date: Jun. 26, 2019

(87) PCT Pub. No.: WO2018/120873
PCT Pub. Date: Jul. 5, 2018

(65) Prior Publication Data
US 2019/0329173 A1    Oct. 31, 2019

(30) Foreign Application Priority Data
Dec. 27, 2016  (CN) .......................... 201611227156.9

(51) Int. Cl.
*A61M 39/20* (2006.01)
*A61M 5/158* (2006.01)
(Continued)

(52) U.S. Cl.
CPC ............ *A61M 39/20* (2013.01); *A61M 5/158* (2013.01); *A61M 5/165* (2013.01); *B01D 46/543* (2013.01);
(Continued)

(58) Field of Classification Search
CPC .......... A61M 5/165; A61M 2005/1657; A61M 2205/7545; A61M 2039/205
See application file for complete search history.

(56) References Cited

U.S. PATENT DOCUMENTS

2011/0009717 A1* 1/2011 Davis ............... A61B 5/150992
                                                600/573
2011/0212294 A1* 9/2011 Kato ..................... A61M 39/10
                                                156/290

FOREIGN PATENT DOCUMENTS

CN      203694250 U   *  7/2014
CN      104288874 A   *  1/2015  .............. A61M 5/38
(Continued)

OTHER PUBLICATIONS

Google Patent for CN204246597 as English Translation. Acquired on Jun. 2022. (Year: 2022).*
(Continued)

*Primary Examiner* — Jenna Zhang

(57) ABSTRACT

A device for preventing contamination of a positive-pressure connector (6) of an indwelling needle and a method based on same. The device comprises a shell (1), a connecting port (3) fixedly connected to the shell (1) and used for connecting to the positive-pressure connector (6), an air pressure balance hole (5) disposed opposite to the connecting port (3) and (Continued)

provided on the shell (1), and a filtering membrane (2) provided between the air pressure balance hole (5) and the connecting port (3). The device is simple in structure, adopts a structural design of the filtering membrane (2), can filter microorganisms, bacteria, viruses, dusts, and particulate pollution sources, and is used during indwelling of infusion intervals to prevent the positive-pressure connector (6) from being exposed to the air and maintain the aseptic state and positive-pressure condition of the positive-pressure connector (6) during indwelling.

4 Claims, 2 Drawing Sheets

(51) Int. Cl.
*A61M 5/165* (2006.01)
*B01D 46/54* (2006.01)
*B01D 46/62* (2022.01)

(52) U.S. Cl.
CPC ..... *B01D 46/62* (2022.01); *A61M 2005/1657* (2013.01); *A61M 2205/3344* (2013.01); *A61M 2205/7509* (2013.01); *A61M 2205/7518* (2013.01); *A61M 2205/7545* (2013.01); *B01D 2279/35* (2013.01)

(56) References Cited

FOREIGN PATENT DOCUMENTS

CN   204246597 U   *   4/2015
CN   104606739 A   *   5/2015

OTHER PUBLICATIONS

Google Patent for CN203694250 as English Translation. Acquired on Jun. 2022. (Year: 2022).*
English Translation for CN 104606739. Acquired on Nov. 2022. (Year: 2022).*
English Translation for CN 104288874. Acquired on Nov. 2022. (Year: 2022).*

* cited by examiner

DEVICE FOR PREVENTING CONTAMINATION OF POSITIVE-PRESSURE CONNECTOR OF INDWELLING NEEDLE AND METHOD BASED ON SAME

CROSS REFERENCES TO RELATED APPLICATIONS

This is a Sect. 371 National Stage of PCT International Application No. PCT/CN2017/099018, filed on 25 Aug. 2017, which claims priority of a Chinese Patent Application No. 2016112271569 filed on 27 Dec. 2016, the contents of both applications hereby being incorporated by reference in their entireties for all purposes.

BACKGROUND OF THE PRESENT DISCLOSURE

Field of Disclosure

The present disclosure relates to the technical field of medical devices, and relates to a device for preventing contamination of a positive-pressure connector of an indwelling needle and a method based on same.

Description of Related Arts

The positive-pressure connector is not a disposable product. Replacement of the positive-pressure connector is generally based on the replacement period of an indwelling needle. During continuous infusion of a patient, the positive-pressure connector is easily contaminated after one infusion. At present, medical workers wrap the interface of the positive-pressure connector with sterile gauze after infusion to prevent the interface of the positive-pressure connector from being contaminated, and before re-infusion, the medical staff wipe the interface of the positive-pressure connector with 70%-75% alcohol, and then connect the positive-pressure connector to an infusion system after natural drying. Such an operation not only complicates the process, but also increases the labor intensity of the medical staff, and the interface of the positive-pressure connector still has the possibility of being contaminated by microorganisms, chemicals and dust particles in the air. The reasons are as follows: (1) wrapping the interface of the positive-pressure connector with the sterile gauze does not prevent the microorganisms, chemicals and dust particles in the air from depositing on the interface of the positive-pressure connector; (2) 70%-75% alcohol can only kill bacteria, but cannot kill spores and viruses; if iodophor is used for disinfection, although it can kill bacterial propagules, spores, fungi, protozoa and some viruses, iodophor does not volatilize, and is easily decomposed in light, causing chemical reagents to remain on the interface of the positive-pressure connector, and such chemical reagents introduced into the body during infusion can cause allergic reactions; and (3) a positive-pressure valve of the positive-pressure connector has a joint with the inner wall of shell of the positive-pressure connector, and some positive-pressure valves are also provided with linear or cross-shaped guide grooves; these narrow spaces often cause retention of drugs, microorganisms or impurities; even if wiped with 70%-75% alcohol, the narrow spaces are difficult to clean and cause a potential risk to the patients during infusion.

SUMMARY OF THE PRESENT DISCLOSURE

The present disclosure provides a device for preventing contamination of a positive-pressure connector of an indwelling needle, which is economical and practical, and convenient in operation.

The present disclosure further provides a method based on the device for preventing contamination of a positive-pressure connector of an indwelling needle.

The present disclosure can be achieved by the following technical solutions:

Disclosed is a device for preventing contamination of a positive-pressure connector of an indwelling needle, including a shell, a connecting port fixedly connected to the shell and used for connecting to the positive-pressure connector, an air pressure balance hole disposed opposite to the connecting port and provided on the shell, and a filtering membrane disposed between the air pressure balance hole and the connecting port.

One or more air pressure balance holes are provided, and one or more filtering membranes are provided.

The air pressure balance hole is at the top of the shell, the filtering membrane is a single layer filtering membrane and is clinging to the bottom of the air pressure balance hole, and the connecting port is internally provided with an internal thread adapted to an external thread of the positive-pressure connector.

The air pressure balance hole is at the top of the shell; the filtering membrane includes a primary filtering membrane clinging to the bottom of the air pressure balance hole and a second filtering membrane directly below the primary filtering membrane; and the connecting port is internally provided with an internal thread adapted to an external thread of the positive-pressure connector.

The top of the shell is provided with an upward convex part; the air pressure balance hole is at the convex part; the filtering membrane includes a primary filtering membrane clinging to the bottom of the air pressure balance hole, and a second filtering membrane and a third filtering membrane sequentially disposed from the top to the bottom below the primary filtering membrane; the third filtering membrane is clinging to the top of the connecting port; and the connecting port is internally provided with an internal thread adapted to an external thread of the positive-pressure connector.

The top of the shell is provided with a downward groove; the air pressure balance hole is at the groove; the interior of the shell is provided with an upward convex platform; the filtering membrane includes a primary filtering membrane clinging to the bottom of the air pressure balance hole and a second filtering membrane laid on the platform; and the connecting port is internally provided with an internal thread adapted to an external thread of the positive-pressure connector.

The air pressure balance hole is at the side wall of the shell; the interior of the shell is provided with an upward convex platform; the filtering membrane includes a primary filtering membrane laid on the platform and a second filtering membrane disposed between the primary filtering membrane and the connecting port; and the connecting port is internally provided with an internal thread adapted to an external thread of the positive-pressure connector.

The platform is provided with an air vent which can conduct air in upper and lower cavities.

The shape of the air vent includes, but is not limited to, a circle, an ellipse, a square, a rectangle, or a triangle.

At least one air vent is provided.

The air pressure balance hole is at the top of the shell; the filtering membrane includes a primary filtering membrane clinging to the bottom of the air pressure balance hole and a second filtering membrane clinging to the top of the connecting port; and the connecting port is internally provided with an internal thread adapted to an external thread of the positive-pressure connector.

The pore diameter of the filtering membrane is from a nanometer to a micrometer, and the filtering membrane includes, but is not limited to, a polyethersulfone membrane, a cellulose filter membrane, a nuclear track membrane, an ion-exchange membrane, a nylon membrane, a polytetrafluoroethylene membrane, a polyvinylidene fluoride membrane, or a polypropylene membrane.

The filtering membrane can be made of the same material or different materials.

The pore diameter of the filtering membrane is 0.02-2 μm.

In a preferred technical solution, the filtering membrane has a pore diameter of 0.22 μm.

The shape of the shell includes, but is not limited to, a cylindrical shape, a spherical shape, an ellipsoidal shape, a rectangular shape, a gourd shape, an upper convex lower flat shape, an upper flat lower convex shape, an upper large lower small shape, or an upper small lower large shape. The pore diameter of the air pressure balance hole is from a nanometer to a millimeter, and the shape of the air pressure balance hole includes, but is not limited to, a circle, an ellipse, a square, a rectangle, or a triangle.

The material of the shell, the filtering membrane and the connecting port shall be a polymer material suitable for medical use or an inorganic material suitable for medical use.

In a preferred technical solution, the material of the shell and the connecting port includes, but is not limited to, polypropylene, nylon, polyethylene, polystyrene, polycarbonate, a copolymer of acrylonitrile-butadiene-styrene, polyvinylidene fluoride, polytetrafluoroethylene or polyvinyl chloride.

The shell and the connecting port may be made of the same material or different materials.

The device for preventing contamination of a positive-pressure connector of an indwelling needle is insulated from pollution sources by a filtering membrane and maintains the positive-pressure condition through the air pressure balance hole. The filtering membrane can effectively filter microorganisms, bacteria, viruses, dusts and particulate matter, and the positive-pressure connector exchanges air with the outside through the air pressure balance hole to achieve a positive-pressure condition. The device is provided with an adapted connecting port, which is compatible with all screw or non-screw positive-pressure connectors.

In actual structural design, the air pressure balance hole can be disposed at any position of the shell, but the air pressure balance hole and the positive-pressure connector need to be isolated by at least one filtering membrane. The air pressure balance hole can be disposed at the side wall, the top, a convex part or a recess of the shell.

The present disclosure further provides a method based on the device for preventing contamination of a positive-pressure connector of an indwelling needle, comprising: providing a filtering membrane between the air pressure balance hole and the connecting port, and isolating and filtering microorganisms, bacteria, viruses, dusts and particulate pollution sources through the filtering membrane. The inner cavity of the shell is in communication with the outside through the air pressure balance hole to achieve air exchange, and ensure that the device is in a positive-pressure state.

In practical application, the device consistent with the present disclosure is used during indwelling of infusion intervals to prevent a positive-pressure connector from being exposed to the air and maintain the aseptic state of the positive-pressure connector during indwelling of infusion intervals. Since the shell is provided with the air pressure balance hole, air in the device can be exchanged with the outside. When the positive-pressure connector is connected with the device for preventing contamination, the positive pressure effect of the positive-pressure connector can be maintained for a long time. Since the pore diameter of the filtering membrane is from a nanometer to a micrometer, the rejection coefficient is high, and microorganisms, bacteria, viruses, dusts, particulates and the like can be effectively filtered. In the case of preferred two layers of filtering membranes, one of the filtering membranes is preferably disposed clinging to the bottom of the air pressure balance hole to prevent moisture from depositing in the device for preventing contamination. Nursing staff only need to sleeve the positive-pressure connector with the device for preventing contamination consistent with the present disclosure after each infusion, and detach the device for preventing contamination sleeved on the positive-pressure connector in the next infusion to perform conventional infusion. Since the interface of the positive-pressure connector is not exposed to the air, the nursing staff do not need to wipe to disinfect the interface of the positive-pressure connector with alcohol, thereby not only improving the working efficiency of the medical staff, but also preventing the incompletely disinfected positive-pressure connector from contaminating drugs in an infusion process, which may result in accidents in patients.

The device consistent with the present disclosure is economical and practical, adopts a structural design of a filtering membrane, can filter microorganisms, bacteria, viruses, dusts, particulates and other suspicious pollution sources, and is used during indwelling of infusion intervals to prevent a positive-pressure connector from being exposed to the air and maintain the aseptic state and positive-pressure condition of the positive-pressure connector during indwelling of infusion intervals. Operation of wrapping the positive-pressure connector with sterile gauze after an infusion and operation of wiping the positive-pressure connector with alcohol before reinfusion by medical staff are omitted, thereby improving the working efficiency of medical staff.

DESCRIPTION OF MARKS IN THE FIGURES

1—shell, 2—single layer filtering membrane, 2a—primary filtering membrane, 2b—second filtering membrane, 2c—third filtering membrane, 3—connecting port, 4—internal thread, 5—air pressure balance hole, 6—positive-pressure connector.

DETAILED DESCRIPTION OF THE PREFERRED EMBODIMENTS

The wide application of intravenous indwelling needles not only greatly reduces pain caused by repeated punctures in patients' long-term treatment, but also reduces the workload of nursing. In particular, the intravenous indwelling needle with a positive-pressure connector can prevent the medical staff from being pricked by needles because needles are not needed, thereby ensuring the personal safety of the nursing staff.

Disclosed is an anticontamination structure of a positive-pressure connector of a medical indwelling needle, which is technically characterized in that one end is closed and the other end forms a cylindrical interface cap with an internal thread, and the internal thread at the end of the interface cap can be tightly connected to the external thread of the positive-pressure connector. Although the utility model patent can prevent the positive-pressure connector from being exposed, the utility model allows the positive-pressure connector to be in a closed space, which destroys the positive-pressure condition of the positive-pressure connector.

Disclosed is a protective cap for preventing contamination of a positive-pressure connector of a medical indwelling needle, which is technically characterized in that the protective cap includes a cap and a tubular cap wall, the tubular cap wall is internally provided with an internal thread adapted to an external thread of the positive-pressure connector, a wiping device is disposed on the cap, and cotton is in the wiping device. After infusion, the protective cap of the utility model is installed on the positive-pressure connector, and before performing infusion again, the wiping device is rotated. The whole operation step is cumbersome, and the built-in cotton cannot completely disinfect the positive-pressure connector.

At present, a membrane isolation method is not used in the technology to prevent contamination of positive-pressure connectors. However, the membrane isolation method is widely used in the production process of pharmaceuticals, especially in the manufacture process of liquid medicines, because filtering membranes can effectively remove bacteria and particles, and the membrane isolation method is safe and reliable.

The present disclosure is explained in detail with reference to the accompanying drawings and specific embodiments.

Embodiment 1

Figure 1:
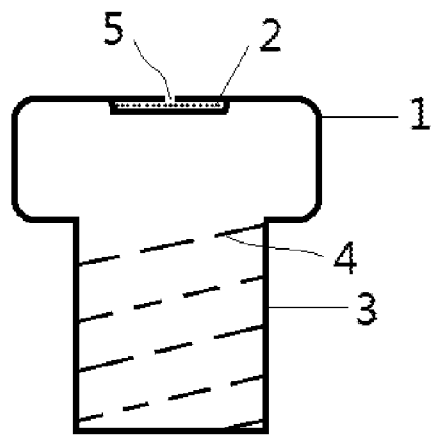
FIG. 1 is a cross-sectional view of Embodiment 1.

As shown in FIG. 1, the device according to this embodiment includes a shell 1, a single layer filtering membrane 2 and a connecting port 3. The connecting port 3 is internally provided with an internal thread 4 adapted to an external thread of a positive-pressure connector 6, an air pressure balance hole 5 is disposed at the top of the shell 1, and the single layer filtering membrane 2 is clinging to the bottom of the air pressure balance hole 5.

In this embodiment, the pore diameter of the filtering membrane is from a nanometer to a micrometer, and the filtering membrane includes, but is not limited to, a polyethersulfone membrane, a cellulose filter membrane, a nuclear track membrane, an ion-exchange membrane, a nylon membrane, a polytetrafluoroethylene membrane, a polyvinylidene fluoride membrane, or a polypropylene membrane.

When structural design is performed, the shape of the shell 1 includes, but is not limited to, a cylindrical shape, a spherical shape, an ellipsoidal shape, a rectangular shape, a gourd shape, an upper convex lower flat shape, an upper flat lower convex shape, an upper large lower small shape, or an upper small lower large shape.

The pore diameter of the air pressure balance hole 5 is from a nanometer to a millimeter, and the shape of the air pressure balance hole 5 includes, but is not limited to, a circle, an ellipse, a square, a rectangle, or a triangle.

The device according to this embodiment is provided with the adapted connecting port 3, which can be connected to the positive-pressure connector 6.

The present disclosure further provides a method based on the device according to this embodiment, a filtering membrane is disposed between an air pressure balance hole and a connecting port, and microorganisms, bacteria, viruses, dusts and particulate pollution sources are isolated and filtered through the filtering membrane. The inner cavity of the shell is in communication with the outside through the air pressure balance hole to achieve air exchange, and ensure that the device is in a positive-pressure state.

Embodiment 2

Figure 2:
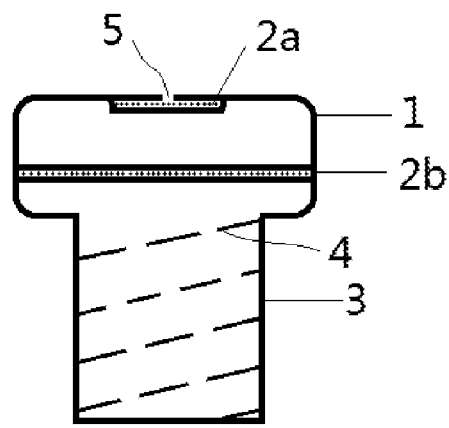
FIG. 2 is a cross-sectional view of Embodiment 2.

As shown in FIG. 2, the device according to this embodiment includes a shell 1, a connecting port 3 fixedly connected to the shell 1 and used for connecting to the positive-pressure connector 6, an air pressure balance hole 5 disposed opposite to the connecting port 3 and provided on the shell 1, and a filtering membrane disposed between the air pressure balance hole 5 and the connecting port 3.

The air pressure balance hole 5 is at the top of the shell 1, and the filtering membrane includes a primary filtering membrane 2a clinging to the bottom of the air pressure balance hole 5 and a second filtering membrane 2b directly below the primary filtering membrane 2a, and the connecting port 3 is internally provided with an internal thread 4 adapted to an external thread of the positive-pressure connector 6.

The rest are the same as in the Embodiment 1.

Embodiment 3

Figure 3:
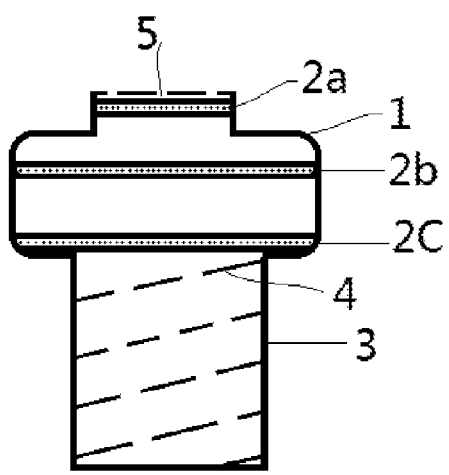
FIG. 3 is a cross-sectional view of Embodiment 3.

As shown in FIG. 3, the device according to this embodiment includes a shell 1, a connecting port 3 fixedly connected to the shell 1 and used for connecting to the positive-pressure connector 6, an air pressure balance hole 5 disposed opposite to the connecting port 3 and provided on the shell 1, and a filtering membrane disposed between the air pressure balance hole 5 and the connecting port 3.

The top of the shell 1 is provided with an upward convex part, and the air pressure balance hole 5 is at the convex part. The filtering membrane includes a primary filtering membrane 2a clinging to the bottom of the air pressure balance hole 5, and a second filtering membrane 2b and a third filtering membrane 2c sequentially disposed from the top to the bottom below the primary filtering membrane 2a. The third filtering membrane 2c is disposed clinging to the top of the connecting port 3, and the connecting port 3 is internally provided with an internal thread 4 adapted to an external thread of the positive-pressure connector 6.

The rest are the same as in Embodiment 1.

Embodiment 4

Figure 4:
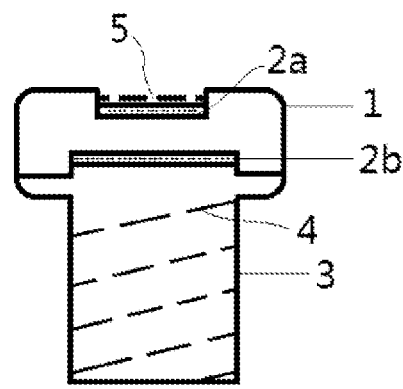
FIG. 4 is a cross-sectional view of Embodiment 4.

As shown in FIG. 4, the device according to this embodiment includes a shell 1, a connecting port 3 fixedly connected to the shell 1 and used for connecting to the positive-pressure connector 6, an air pressure balance hole 5 disposed opposite to the connecting port 3 and provided on the shell 1, and a filtering membrane disposed between the air pressure balance hole 5 and the connecting port 3.

The top of the shell 1 is provided with a downward groove, the air pressure balance hole 5 is at the groove, the interior of the shell 1 is provided with an upward convex platform, the platform is provided with at least one air vent, and the air vent can conduct air in upper and lower cavities. The shape of the air vent includes, but is not limited to, a circle, an ellipse, a square, a rectangle, or a triangle. The filtering membrane includes a primary filtering membrane 2a clinging to the bottom of the air pressure balance hole 5 and a second filtering membrane 2b laid on the platform, and the connecting port 3 is internally provided with an internal thread 4 adapted to an external thread of the positive-pressure connector 6.

The rest are the same as in Embodiment 1.

Embodiment 5

Figure 5:
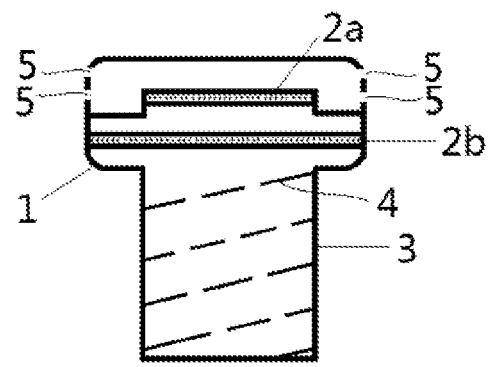
FIG. 5 is a cross-sectional view of Embodiment 5.

As shown in FIG. 5, the device according to this embodiment includes a shell 1, a connecting port 3 fixedly connected to the shell 1 and used for connecting to the positive-pressure connector 6, an air pressure balance hole 5 provided on the shell 1, and a filtering membrane disposed between the air pressure balance hole 5 and the connecting port 3.

The air pressure balance hole 5 is at the side wall of the shell 1, the interior of the shell 1 is provided with an upward convex platform, the platform is provided with at least one air vent, and the air vent can conduct air in upper and lower cavities. The shape of the air vent includes, but is not limited to, a circle, an ellipse, a square, a rectangle, or a triangle. The filtering membrane includes a primary filtering membrane 2a laid on the platform and a second filtering membrane 2b disposed between the primary filtering membrane 2a and the connecting port 3, and the connecting port 3 is internally provided with an internal thread 4 adapted to the external thread of the positive-pressure connector 6.

The rest are the same as in Embodiment 1.

Embodiment 6

Figure 6:
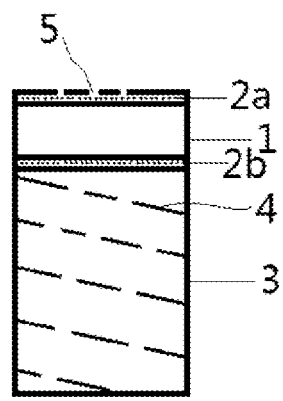
FIG. 6 is a cross-sectional view of Embodiment 6.

As shown in FIG. 6, the device according to this embodiment includes a shell 1, a connecting port 3 fixedly connected to the shell 1 and used for connecting to the positive-pressure connector 6, an air pressure balance hole 5 disposed opposite to the connecting port 3 and provided on the shell 1, and a filtering membrane disposed between the air pressure balance hole 5 and the connecting port 3.

The air pressure balance hole 5 is at the top of the shell 1, the filtering membrane includes a primary filtering membrane 2a clinging to the bottom of the air pressure balance hole 5 and a second filtering membrane 2b clinging to the top of the connecting port 3, and the connecting port 3 is internally provided with an internal thread 4 adapted to an external thread of the positive-pressure connector 6.

The rest are the same as in Embodiment 1.

Embodiment 7

Figure 7:
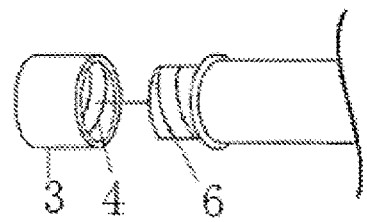
FIG. 7 is a schematic structural diagram of an assembly of a device and a positive-pressure connector consistent with the present disclosure.

As shown in FIG. 7, an internal thread 4 of a device according to this embodiment is connected to an external thread of a positive-pressure connector 6.

The rest are the same as in Embodiment 3.

After an infusion, the device is installed at the interface end of the positive-pressure connector 6 through the connecting port 3, to prevent the interface of the positive-pressure connector 6 from being contaminated by potential contaminants due to long-time exposure to the air. At the next infusion, the anticontamination device sleeved on the positive-pressure connector 6 is detached, and then conventional infusion can be performed. Since the air pressure balance hole 5 is on the shell 1 of the device, the positive pressure effect can be maintained for a long time. Since the rejection coefficient of the filtering membrane is high, microorganisms, dusts, particulate matter and the like can be effectively filtered and cannot contaminate the interface of the positive-pressure connector 6. Due to the design of the multilayer filtering membrane, deposition of moisture in the air in the shell 1 can be avoided. Since the interface of the positive-pressure connector 6 is not exposed to the air, nursing staff do not need to wipe to disinfect the interface of the positive-pressure connector with alcohol, thereby improving the working efficiency of medical staff.

The above description of the embodiments is intended to facilitate the understanding and use of the present disclosure by persons of ordinary skill in the art. It is apparent to those skilled in the art that various modifications can be readily made to these embodiments and the general principles described herein can be applied to other embodiments without creative efforts. Accordingly, the present disclosure is not limited to the embodiments described above, and all modifications and variations made by those skilled in the art within the scope of the present disclosure should fall within the scope of the present disclosure.

What is claimed is:
1. A device for preventing contamination of a positive-pressure connector of an indwelling needle, comprising:
    a shell;
    a connecting port fixedly connected to the shell and used for connecting to the positive-pressure connector;
    an air pressure balance hole disposed opposite to the connecting port and provided on the shell; and
    a plurality of filtering membranes disposed between the air pressure balance hole and the connecting port;
    among the plurality of filtering membranes, the filtering membrane closest to the air pressure balance hole is a primary filtering membrane, wherein the primary filtering membrane is separated from the other filtering membranes;
    wherein a top of the shell is provided with an upward convex part;
    the air pressure balance hole is at the upward convex part;
    the plurality of filtering membranes comprises:
        the primary filtering membrane clinging to a bottom of the air pressure balance hole; and
        a second filtering membrane and a third filtering membrane sequentially provided from top to bottom below the primary filtering membrane, wherein the third filtering membrane is clinging to a top of the connecting port; and
        the connecting port is internally provided with an internal thread adapted to an external thread of the positive-pressure connector.

2. The device for preventing contamination of the positive-pressure connector of the indwelling needle according to claim 1, wherein
a pore diameter of the plurality of filtering membranes is 0.02-2 μm, and the plurality of filtering membranes comprises a polyethersulfone membrane, a cellulose filter membrane, a nuclear track membrane, an ion-exchange membrane, a nylon membrane, a polytetrafluoroethylene membrane, a polyvinylidene fluoride membrane, or a polypropylene membrane;
the shape of the shell comprises a cylindrical shape, a spherical shape, an ellipsoidal shape, a rectangular shape, a gourd shape, an upper convex lower flat shape, an upper flat lower convex shape, an upper large lower small shape, or an upper small lower large shape;
the diameter of the air pressure balance hole is from a nanometer to a millimeter, and the shape of the air pressure balance hole comprises a circle, an ellipse, a square, a rectangle, or a triangle.

3. A method using a device for preventing contamination of a positive-pressure connector of an indwelling needle,
wherein the device is comprises: a shell, a connecting port fixedly connected to the shell and used for connecting to the positive-pressure connector, an air pressure balance hole disposed opposite to the connecting port and provided on the shell, and a plurality of filtering membranes disposed between the air pressure balance hole and the connecting port, wherein among the plurality of filtering membranes, the filtering membrane closest to the air pressure balance hole is a primary filtering membrane, wherein the primary filtering membrane is separated from the other filtering membranes; wherein the method comprises:
providing the plurality of filtering membranes between the air pressure balance hole and the connecting port; and
isolating and filtering microorganisms, bacteria, viruses, dusts and particulate pollution sources through the plurality of filtering membranes, wherein
an inner cavity of the shell is in communication with the outside through the air pressure balance hole to achieve air exchange, and ensure that the device is in a positive-pressure state;
wherein a top of the shell is provided with an upward convex part;
the air pressure balance hole is at the upward convex part;
the plurality of filtering membranes comprises:
the primary filtering membrane clinging to a bottom of the air pressure balance hole; and
a second filtering membrane and a third filtering membrane sequentially provided from top to bottom below the primary filtering membrane, wherein
the third filtering membrane is clinging to a top of the connecting port; and
the connecting port is internally provided with an internal thread adapted to an external thread of the positive-pressure connector.

4. A device for preventing contamination of a positive-pressure connector of an indwelling needle, comprising:
a shell;
a connecting port fixedly connected to the shell and used for connecting to the positive-pressure connector;
a plurality of air pressure balance holes disposed opposite to the connecting port and provided on the shell; and
a plurality of filtering membranes disposed between the plurality of air pressure balance holes and the connecting port;
among the plurality of filtering membranes, the filtering membrane of the plurality of filtering membranes that is positioned closest to more of the plurality of air pressure balance holes is a primary filtering membrane, wherein the primary filtering membrane is separated from the other filtering membranes;
wherein a top of the shell is provided with an upward convex part;
the air pressure balance hole is at the upward convex part;
the plurality of filtering membranes comprises:
the primary filtering membrane clinging to a bottom of the air pressure balance hole; and
a second filtering membrane and a third filtering membrane sequentially provided from top to bottom below the primary filtering membrane, wherein
the third filtering membrane is clinging to a top of the connecting port; and
the connecting port is internally provided with an internal thread adapted to an external thread of the positive-pressure connector.

\* \* \* \* \*